US00PP15168P2

(12) United States Plant Patent
Chou et al.

(10) Patent No.: US PP15,168 P2
(45) Date of Patent: Sep. 21, 2004

(54) IMPATIENS PLANT NAMED 'BALFUSGLO'

(50) Latin Name: ***Impatiens walleriana*×*Impatiens auricoma***
Varietal Denomination: Balfusglo

(75) Inventors: Tau San Chou, Batavia, IL (US); Kristen Nicole Gross, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 14 days.

(21) Appl. No.: 10/736,735

(22) Filed: Dec. 16, 2003

(51) Int. Cl.[7] ..... A01H 5/00
(52) U.S. Cl. ..... Plt./317
(58) Field of Search ..... Plt./317

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct cultivar of Impatiens plant named 'Balfusglo', characterized by its single, cupped, yellow-colored flowers, medium green-colored foliage, upright and mounded habit, and excellent basal branching.

1 Drawing Sheet

BACKGROUND OF THE INVENTION

The present invention relates to a new and distinct Impatiens plant botanically known as *Impatiens walleriana*× *Impatiens auricoma* and hereinafter referred to by the cultivar name 'Balfusglo'.

The new cultivar was developed by the inventors in a controlled breeding program during September 1999 at Elburn, Ill. The objective of the breeding program was to develop Impatiens cultivars with numerous flowers, new and unique flower shape and colors, excellent basal branching, and upright compact to moderate growth habit.

The female (seed) parent of 'Balfusglo' was the proprietary *Impatiens walleriana* selection designated '9516-4' (not patented) characterized by its upright growth habit, coral-colored flowers, and medium green-colored foliage. The male (pollen) parent of 'Balfusglo' was the proprietary *Impatiens auricoma* selection designated '193' (not patented) characterized by its upright growth habit, yellow-colored flowers, and dark green-colored foliage. 'Balfusglo' was discovered and selected as a single flowering plant within the progeny of the above stated cross-pollination in August of 2000 at Elburn, Ill. and initially designated 'PAS T31-08'.

Asexual reproduction of the new cultivar by shoot tip or stem cuttings since August 2000 at Elburn, Ill. and West Chicago, Ill., has demonstrated that the new cultivar reproduce true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits single, cupped, yellow-colored flowers,
2. Forms medium green-colored foliage, 3. Exhibits a good basal branching character, and
4. Exhibits an upright mounded growth habit.

Plants of the new cultivar differ from plants of the female parent primarily in flower color, flower shape and leaf shape, and from plants of the male parent in flower color, flower shape, leaf size, and branching habit.

Plants of the new cultivar can be compared to plants of '96-009-7' (U.S. Plant Pat. No. 10,972). However, in a side-by-side comparison conducted in West Chicago, Ill., plants of the new cultivar differed from plants of '96-009-7' primarily in the following characteristics:

1. Plants of the new cultivar have a more compact growth habit than plants of '96-009-7', and
2. Plants of the new cultivar have larger flowers than plants of '96-009-7'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describe the colors of 'Balfusglo'. The plants were grown for 13 weeks in a greenhouse at West Chicago, Ill.

DETAILED DESCRIPTION

Figure 1:
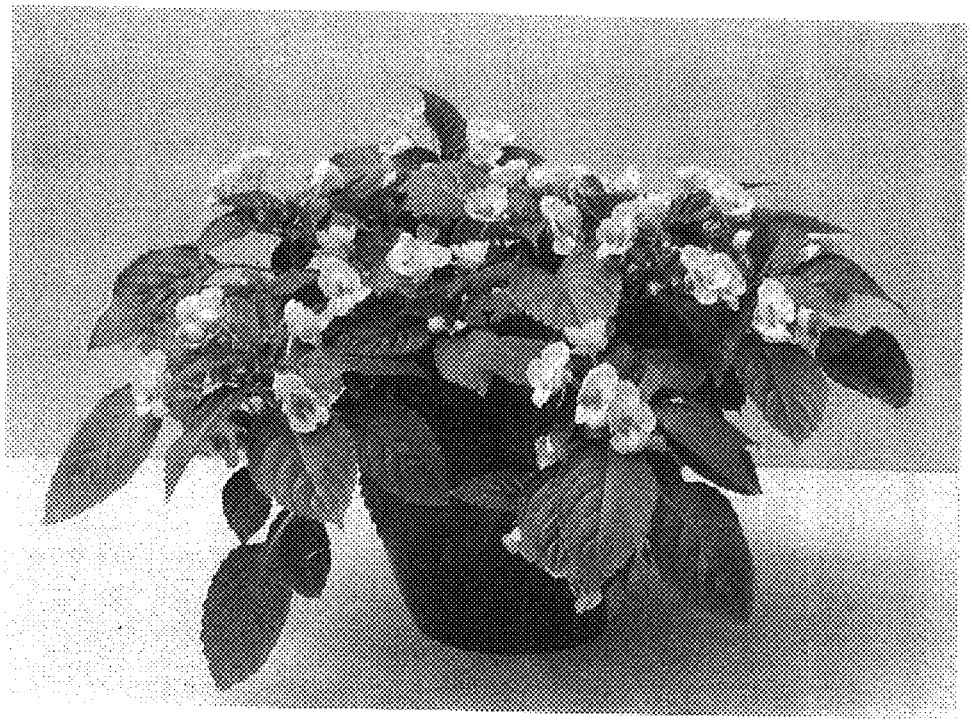
FIG. 1 illustrates a side view of the overall growth and flowering habit of 'Balfusglo'.
Figure 2:
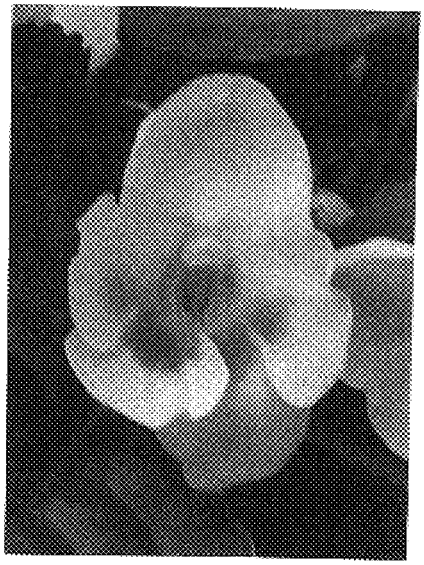
FIG. 2 illustrates a close-up view of a single flower of 'Balfusglo'.

The chart used in the identification of colors described herein is The R.H.S. Colour Chart of The Royal Horticultural Society, London, England, 1995 edition, except where general color terms of ordinary significance are used. The color values were determined on Sep. 3, 2003 between 9:00 and 10:45 a.m. under natural light conditions.

The following measurements and comparisons describe plants produced from shoot tip or stem cuttings taken from stock plants and grown under greenhouse conditions comparable to those used in commercial practice. The plants were grown in 10 cm pots for 15 weeks utilizing a soilless growth medium. Greenhouse temperatures were maintained at approximately 72° F. during the day and approximately 65° F. during the night. Greenhouse light levels were maintained at approximately 4,000 to 6,000 footcandles during the day.

Botanical classification: *Impatiens wallerianaxImpatiens auricoma* cultivar 'Balfusglo'.

Parentage:

*Female (seed) parent.*—Proprietary *Impatiens walleriana* selection designated '9516-4' (not patented).

*Male (pollen) parent.*—Proprietary *Impatiens auricoma* selection designated '193' (not patented).

Propagation:

*Type cutting.*—Shoot tip or stem (with two nodes).

*Time to initiate roots.*—Approximately 7–14 days.

*Time to develop a rooted cutting.*—Approximately 21 days.

*Root description.*—Fine, fibrous.

*Rooting habit.*—Freely branching.

Plant description:

*Habit of growth.*—Moderately vigorous with good basal branching. A mature plant, 15 weeks after the planting of a rooted cutting, commonly measures approximately 25.8 cm in height and approximately 42.1 cm in width.

*Plant form.*—Upright and mounded.

*Lateral branches.*—Quantity: Approximately 4. Length: Approximately 19.9 cm. Diameter: Approximately 8 mm. Texture: Glabrous. Color: 146C with streaks of 187B especially at nodes. Internode length at center of branch: Approximately 3.3 cm.

*Foliage.*—Type: Simple. Arrangement of lower leaves: Alternate. Arrangement of upper leaves: Whorls. Shape: Elliptic. Apex: Acuminate/cuspidate. Base: Attenuate. Margin: Crenate with ciliation. Texture of upper and lower surface: Glabrous. Venation pattern: Pinnate, arcuate. Size of mature foliage: Length: Approximately 8 cm. Width: Approximately 3.7 cm. Color of mature foliage: Upper surface: 137A with veins and mid-vein of 146D. Lower surface: 147B with veins and mid-vein of 146D. Petiole: Diameter: Approximately 2 mm. Length: Approximately 2.3 cm with 2 mm stipules along edges. Texture: Upper and lower surface: Glabrous. Color: Upper and lower surface: 146D with overlay of 187D.

Flower description:

*Flower type.*—Single, not fragrant with self-cleaning petals.

*Flowering habit.*—Freely flowering with flowers positioned above the foliage and facing outward.

*Natural flowering season.*—Year round in greenhouse environment. Flowering is continuous from spring until fall in the garden.

*Flower longevity on plant.*—Approximately 5 days.

*Quantity of flowers.*—Approximately 5 flowers and 5 buds per stem at any one time.

*Mature flower buds (just before opening).*—Shape: Ovate. Length: Approximately 1.3 cm. Diameter: Approximately 9.4 mm. Texture: Glabrous. Color: 15D.

*Flower shape.*—Oval, cupped when first open, becoming more flat with age.

*Flower size.*—Length: Approximately 3.8 cm. Width: Approximately 3.3 cm. Depth: Approximately 1.2 cm.

*Petals.*—Number: Five per flower. Texture: Glabrous. Appearance: Iridescent.

*Superior petal.*—Length: Approximately 1.3 cm. Width: Approximately 1.2 cm. Shape: Cucullate. Margin: Entire. Apex: Emarginate. Base: Truncate. Color of upper surface: 9D. Color of lower surface: 9D.

*Lateral petals.*—Length: 1.6 cm. Width: 1.4 cm. Shape: Obovate. Margin: Entire. Apex: Obtuse. Base: Attenuate. Color of upper surface: 9D with faint spot of 32B and veins of 46A along inner edge. Color of lower surface: 9D.

*Lower petals.*—Length: 2.2 cm. Width: 1.2 cm. Shape: Obovate. Margin: Entire. Apex: Obtuse. Base: Attenuate. Color of upper surface: 9D with center of petal having a small area of 32B. Color of lower surface: 9D.

*Peduncles.*—Strength: Strong. Angle to stem: Acute. Length: Approximately 2.6 cm. Diameter: Approximately 1 mm. Texture: Glabrous. Color: 144B.

*Calyx.*—Consists of 3 sepals. Lateral sepals: Length: Approximately 8 mm. Width: Approximately 5 mm. Texture: Glabrous. Color of both surfaces: 1D with tip of 144C. Lower sepal: Length: Approximately 1.4 cm. Width: Approximately 9 mm. Texture: Glabrous. Color of both surfaces: 1D with tip of 144C. Base of lower sepal is modified to form spur.

*Spur.*—Quantity: One per flower. Double tipped. Length: Approximately 1.5 cm. Diameter at flower: Approximately 2 mm. Diameter of tips: Approximately 1 mm. Aspect: Moderately curved downward. Color: 1C.

*Reproductive organs.*—Androecium: Five stamens, anthers are fused together forming one organ that surrounds the pistil. Filament color: 1C. Anther shape: Oval. Anther length: Approximately 2 mm. Anther color: Lighter than 35D. Gynoecium: Pistil number: One per flower. Pistil length: 6 mm. Stigma shape: Five pointed star. Stigma length: 0.5 mm. Stigma color: Colorless, translucent. Style length: 1.5 mm. Style color: Colorless, translucent. Ovary length: 4 mm. Ovary diameter: 2 mm. Ovary texture: Glabrous. Ovary color: 149A.

Seed and fruit development: Neither seed nor fruit production has been observed.

Disease and pest resistance: Resistance to pathogens and pests common to Impatiens has not been observed.

What is claimed is:

1. A new and distinct cultivar of Impatiens plant named 'Balfusglo' substantially, as herein shown and described, which:

1. Exhibits single, cupped, yellow-colored flowers,
2. Forms medium green-colored foliage,
3. Exhibits a good basal branching characer, and
4. Exhibits an upright and mounded growth habit.

* * * * *